United States Patent [19]

Schnurr et al.

[11] Patent Number: 5,679,869

[45] Date of Patent: Oct. 21, 1997

[54] PREPARATION OF ALDEHYDES

[75] Inventors: Werner Schnurr, Herxheim; Rolf Fischer, Heidelberg; Joachim Wulff-Döring, Frankenthal; Michael Hesse, Schifferstadt, all of Germany

[73] Assignee: BASF Aktiengesellschaft, Ludwigshafen, Germany

[21] Appl. No.: 567,749

[22] Filed: Dec. 5, 1995

[30] Foreign Application Priority Data

Dec. 8, 1994 [DE] Germany ............... 44 43 704.8

[51] Int. Cl.⁶ .................................................. C07C 45/41
[52] U.S. Cl. .................... 568/484; 568/435; 568/490; 568/485; 564/305; 564/453; 564/455
[58] Field of Search .................. 568/435, 484, 568/490, 485; 502/103, 302; 564/305, 453, 455, 463

[56] References Cited

U.S. PATENT DOCUMENTS

| | | | |
|---|---|---|---|
| 3,935,265 | 1/1976 | Feinstein et al. | |
| 4,328,373 | 5/1982 | Strojny | 568/435 |
| 4,585,899 | 4/1986 | Gelbein et al. | |
| 4,585,900 | 4/1986 | Holy et al. | |
| 4,950,799 | 8/1990 | Hargis | |
| 4,987,265 | 1/1991 | Van Geem | 568/435 |
| 5,059,716 | 10/1991 | Joentgen et al. | |
| 5,239,108 | 8/1993 | Yokoyama | 560/126 |
| 5,306,845 | 4/1994 | Yokohama et al. | |
| 5,334,769 | 8/1994 | Ferrero et al. | |
| 5,393,793 | 2/1995 | Inui | 518/713 |

FOREIGN PATENT DOCUMENTS

| | | |
|---|---|---|
| 101111 | 8/1982 | European Pat. Off. |
| 150961 | 8/1985 | European Pat. Off. |
| 290096 | 4/1991 | European Pat. Off. |
| 439115 | 7/1991 | European Pat. Off. |
| 304853 | 1/1993 | European Pat. Off. |

*Primary Examiner*—C. Warren Ivy
*Assistant Examiner*—Jean F. Vollano
*Attorney, Agent, or Firm*—John H. Shurtleff

[57] ABSTRACT

A process for preparing aldehydes of the general formula I

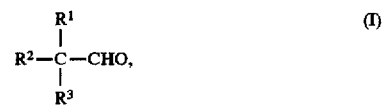

where $R^1$, $R^2$ and $R^3$ are each hydrogen, $C_1$–$C_6$-alkyl, $C_3$–$C_8$-cycloalkyl, aryl, $C_7$–$C_{12}$-alkylphenyl, $C_7$–$C_{12}$-phenylalkyl and $R^1$ and $R^2$ are joined together to form a 3-, 4-, 5-, 6- or 7-membered cycloaliphatic ring, $R^1$ and $R^3$ are each $C_1$–$C_4$-alkoxy, phenoxy, methylamino, dimethylamino or halogen, and $R^1$ is additionally hydroxyl or amino comprises reacting a carboxylic acid or ester of the general formula II

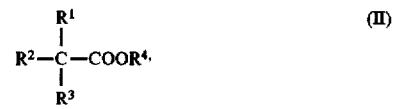

where $R^1$, $R^2$ and $R^3$ are each as defined above, and $R^4$ is hydrogen, $C_1$–$C_6$-alkyl, $C_3$–$C_8$-cycloalkyl, aryl, $C_7$–$C_{12}$-alkylphenyl or $C_7$–$C_{12}$-phenylalkyl, with hydrogen in the gas phase at temperatures from 200° to 450° C. and pressures from 0.1 to 20 bar in the presence of a catalyst whose catalytically active mass comprises from 60 to 99.9% by weight of zirconium oxide and from 0.1 to 40% by weight of one or more elements of the lanthanides.

9 Claims, No Drawings

PREPARATION OF ALDEHYDES

The present invention relates to a process for preparing aldehydes by reacting the corresponding carboxylic acids or esters with hydrogen in the gas phase in the presence of catalysts comprising zirconium oxide and elements of the lanthanides.

It is known to convert carboxylic acids such as benzoic acid or cyclohexanecarboxylic acid or their esters into the corresponding aldehydes by hydrogenation in the gas phase.

U.S. Pat. No. 3,935,265 discloses that it is possible to hydrogenate alkyl esters of aromatic carboxylic acids with hydrogen over $Al_2O_3$ at from 400° to 600° C. For example, methyl benzoate is converted into benzaldehyde with a selectivity of 37% (conversion: 39%). Other catalysts used for the hydrogenation of aromatic and aliphatic carboxylic acids include, for example, Ru/Sn (EP-A-539 274), manganese oxide (EP-A-290 096, U.S Pat. No. 4,585,899), iron oxide (EP-A-304 853), vanadium oxide and/or titanium dioxide (U.S. Pat. No. 4,950,799, EP-A-414065), $Cu/Y_2O_3$ (U.S. Pat. No. 4,585,900), $Cr_2O_3/ZrO_2$ (EP-A-150961, EP 439115), $Cr_2O_3$ (U.S. Pat. No. 5,306,845) or lanthanide oxides/$Al_2O_3$ (U.S. Pat. No. 4,328,373, EP-A-101 111).

The prior art hydrogenation processes produce only unsatisfactory yields and selectivities in most cases, in part because of very high hydrogenation temperatures.

It is an object of the present invention to remedy the aforementioned disadvantages.

We have found that this object is achieved by a novel and improved process for preparing aldehydes of the general formula I

where
R$^1$, R$^2$ and R$^3$ are each hydrogen, $C_1$–$C_6$-alkyl, $C_3$–$C_8$-cycloalkyl, aryl, $C_7$–$C_{12}$-alkylphenyl, $C_7$–$C_{12}$-phenylalkyl and R$^1$ and R$^2$ are joined together to form a 3-, 4-, 5-, 6- or 7-membered cycloaliphatic ring,
R$^1$ and R$^3$ are each $C_1$–$C_4$-alkoxy, phenoxy, methylamino, dimethylamino or halogen, and
R$^1$ is additionally hydroxyl or amino,
which comprises reacting a carboxylic acid or ester of the general formula II

where
R$^1$, R$^2$ and R$^3$ are each as defined above, and
R$^4$ is hydrogen, $C_1$–$C_6$-alkyl, $C_3$–$C_8$-cycloalkyl, aryl, $C_7$–$C_{12}$-alkylphenyl or $C_7$–$C_{12}$-phenylalkyl,
with hydrogen in the gas phase at temperatures from 200° to 450° C. and pressures from 0.1 to 20 bar in the presence of a catalyst whose catalytically active mass comprises from 60 to 99.9% by weight of zirconium oxide and from 0.1 to 40% by weight of one or more elements of the lanthanides.

The process of the present invention can be carried out as follows:

The novel hydrogenation of the carboxylic acid or ester II with hydrogen in the presence of a catalyst whose catalytically active mass comprises from 60 to 99.9, in particular from 80 to 99.9%, by weight of zirconium oxide and from 0.1 to 40, in particular from 0.1 to 20%, by weight of one or more elements of the lanthanides is generally carried out at temperatures from 200° to 450° C., preferably from 250° to 400° C., particularly preferably from 300° to 380° C., and pressures from 0.1 to 20 bar, preferably from 0.7 to 5 bar, particularly preferably at atmospheric pressure. The temperature and pressure required are dependent on the catalyst activity and the thermal stability of precursor and product.

Suitable catalysts include supported catalysts, preferably solid catalysts of zirconium oxide in cubic, tetragonal or monoclinic phase, preferably in monoclinic phase, which have been doped with one or more elements of the lanthanide series. The catalytically active mass comprises in general from 80 to 99.9% by weight, preferably from 90 to 99.9% by weight, particularly preferably from 92 to 99% by weight of zirconium oxide and from 0.1 to 20% by weight of one or more elements of the lanthanides, preferably from 0.1 to 10% by weight of lanthanum, cerium, praseodymium, neodymium, samarium, europium or mixtures thereof, particularly preferably from 1 to 8% by weight of lanthanum (III) oxide. The doping is generally effected by saturating the zirconium oxide with salt solutions (aqueous or alcoholic) of the lanthanides.

The catalyst may additionally include further dopants (e.g. chromium, iron, yttrium, manganese) in amounts from 0.001 to 10% by weight. Preference is given to catalysts without such additions.

The BET surface area of the zirconium oxide can vary within wide limits and is generally from 5 to 150 m$^2$/g, preferably from 20 to 150 m$^2$/g, particularly preferably from 40 to 120 m$^2$/g.

Catalysts of this type are produced in a conventional manner, for example by saturating preformed carrier elements such as pellets, balls or extrudates, drying and calcining.

The preferred supported catalysts are very active over a prolonged period. Deactivated catalysts can be regenerated by treatment with gases containing molecular oxygen, e.g. air, at temperatures from 350° to 500° C.

The weight hourly space velocity over the catalyst is held in general within the range from 0.01 to 10, preferably within the range from 0.01 to 3, kg of carboxylic acid or ester per kg of catalyst per hour.

The hydrogen concentration in the feed gas depends on the carboxylic acid or ester concentration. The molar ratio of hydrogen to carboxylic acid or ester is in general within the range from 2:1 to 100:1, preferably within the range from 10:1 to 70:1. The hydrogen can also come from formic acid used as source.

It can also be advantageous to add an inert diluent. Typically, nitrogen, water or gaseous reaction-inert compounds such as hydrocarbons, aromatics or ethers are employed.

The reaction can be carried out in the gas phase, continuously as a fixed bed reaction with a fixed bed catalyst, for example in an upflow or downflow (trickle) process, or as a fluidized bed reaction with the catalyst in the fluidized state. Preference is given to the use of a fixed bed.

By-products of the hydrogenation, e.g. alcohols, can be recycled into the synthesis to increase the selectivity.

The substituents R$^1$, R$^2$, R$^3$ and R$^4$ in compounds I and II each have independently of the others the following meanings:

R$^1$, R$^2$, R$^3$ and R$^4$:
hydrogen,
$C_1$–$C_6$-alkyl, preferably $C_1$–$C_4$-alkyl such as methyl, ethyl, n-propyl, isopropyl, n-butyl, isobutyl, sec-butyl and tert-butyl, particularly preferably methyl and ethyl, $C_3$–$C_8$-cycloalkyl such as cyclopropyl, cyclobutyl, cyclopentyl, cyclohexyl, cycloheptyl and cyclooctyl, preferably cyclopentyl, cyclohexyl and cyclooctyl, particularly preferably cyclopentyl and cyclohexyl, aryl such as phenyl, 1-naphthyl, 2-naphthyl, 1-anthryl, 2-anthryl and 9-anthryl, preferably phenyl, 1-naphthyl and 2-naphthyl, particularly preferably phenyl, $C_7$–$C_{12}$-alkylphenyl such as 2-methylphenyl, 3-methylphenyl, 4-methylphenyl, 2,4-dimethylphenyl, 2,5-dimethylphenyl, 2,6-dimethylphenyl, 3,4-dimethylphenyl, 3,5-dimethylphenyl, 2,3,4-trimethylphenyl, 2,3,5-trimethylphenyl, 2,3,6-trimethylphenyl, 2,4,6-trimethylphenyl, 2-ethylphenyl, 3-ethylphenyl, 4-ethylphenyl, 2-n-propylphenyl, 3-n-propylphenyl and 4-n-propylphenyl, preferably 2-methylphenyl, 3-methylphenyl, 4-methylphenyl, 2,4-dimethylphenyl, 2,5-dimethylphenyl, 2,6-dimethylphenyl, 3,4-dimethylphenyl and 3,5-dimethylphenyl, particularly preferably 2-methylphenyl, 3-methylphenyl, 4-methylphenyl, $C_7$–$C_{12}$-phenylalkyl such as benzyl, 1-phenethyl, 2-phenethyl, 1-phenyl-propyl, 2-phenyl-propyl, 3-phenyl-propyl, 1-phenyl-butyl, 2-phenyl-butyl, 3-phenyl-butyl and 4-phenyl-butyl, preferably benzyl, 1-phenethyl and 2-phenethyl, particularly preferably benzyl, $R^1$ and $R^3$:

$C_1$–$C_4$-alkoxy such as methoxy, ethoxy, n-propoxy, isopropoxy, n-butoxy, isobutoxy, sec-butoxy and tert-butoxy, preferably methoxy, ethoxy, n-propoxy and isopropoxy, particularly preferably methoxy and ethoxy, phenoxy, methylamino, dimethylamino, halogen such as fluorine, chlorine, bromine and iodine, preferably fluorine, chlorine and bromine, particularly preferably chlorine and bromine, and $R^1$:

hydroxyl, amino, $R^1$ and $R^2$ together a 3-, 4-, 5-, 6-, or 7-membered cycloaliphatic ring such as cyclopropyl, cyclobutyl, cyclopentyl, cyclohexyl and cycloheptyl, preferably cyclopentyl, cyclohexyl and cycloheptyl, particularly preferably cyclopentyl and cyclohexyl, in which case $R^3$ is preferably hydrogen or $C_1$–$C_6$-alkyl.

The starting materials used are carboxylic acids or esters of the formula II, e.g. phenylacetic acid, diphenylacetic acid, triphenylacetic acid, methyl phenylacetate, pivalic acid, isobutyric acid, phenylmethylacetic acid, cyclohexanecarboxylic acid or ester, cyclopentanecarboxylic acid or ester, dimethylhydroxyacetic acid, diphenylchloroacetic acid, dimethylmethoxyacetic acid.

The process of the present invention provides a simple way of selectively preparing previously difficult-to-obtain aldehydes.

Aldehydes I are useful as aromas and flavorings and as intermediates, for example for drugs and crop protection agents (Ullmann's Encyclopedia of Industrial Chemistry, Vol. A3, pages 469 to 474).

EXAMPLES

Catalyst Preparation

Example 1

Monoclinic zirconium dioxide (BET surface area: 53 m²/g) in the form of tablets (catalyst A) was saturated with an aqueous solution of lanthanum nitrate by thorough mixing and the mixture was held at room temperature for 2 h. The catalyst was then dried at 120° C. for 15 hours and then heat-treated at from 400° to 500° C. for from 2 to 4 hours.

The catalyst thus prepared had a lanthanum content of 3% by weight.

Example 2

Hydrogen at 100 l/h was used to vaporize 11 g/h of pivalic acid (as melt) and pass it at 330° C. in the downflow direction through 100 ml (128 g) of catalyst A. The gaseous reaction effluent was condensed in cold traps and analyzed by gas chromatography. The pivaldehyde yield was found to be 98% (conversion 100%). The corresponding alcohol was obtained as a recyclable by-product with a yield of 1%.

Example 3

Example 2 was repeated to react the carboxylic acids and the carboxylic ester of the table below, which also shows the results of the reaction.

TABLE

| Carboxylic acid or ester | Temperature [°C.] | Aldehyde yield [%] | Alcohol yield [%] | Conversion [%] | Selectivitity (incl. alcohol recycle) [%] |
|---|---|---|---|---|---|
| Cyclohexanecarboxylic acid | 330 | 90 | 1 | 97 | 94 |
| 2-Methylpropionic acid | 310 | 68 | — | 83 | 82 |
| Methyl 3,5-dimethyloctanoate | 310 | 43 | 15 | 85 | 61 |

We claim:

1. A process for preparing aldehydes of the general formula I $$R^2-\underset{\underset{R^3}{|}}{\overset{\overset{R^1}{|}}{C}}-CHO, \quad (I)$$

where $R^1$, $R^2$ and $R^3$ are each hydrogen, $C_1$–$C_6$-alkyl, $C_3$–$C_8$-cycloalkyl, aryl, $C_7$–$C_{12}$-alkylphenyl, $C_7$–$C_{12}$-phenylalkyl and $R^1$ and $R^2$ are joined together to form a 3-, 4-, 5-, 6- or 7-membered cycloaliphatic ring, $R^1$ and $R^3$ are each $C_1$–$C_4$-alkoxy, phenoxy, methylamino, dimethylamino or halogen, and $R^1$ is additionally hydroxyl or amino, which comprises reacting a carboxylic acid or ester of the general formula II

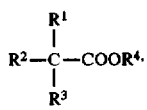

(II)

where

R¹, R² and R³ are each as defined above, and

R⁴ is hydrogen, $C_1$–$C_6$-alkyl, $C_3$–$C_8$-cycloalkyl, aryl, $C_7$–$C_{12}$-alkylphenyl or $C_7$–$C_{12}$-phenylalkyl, with hydrogen in the gas phase at temperatures from 200° to 450° C. and pressures from 0.1 to 20 bar in the presence of a catalyst whose catalytically active mass comprises from 60 to 99.9% by weight of zirconium oxide and from 0.1 to 40% by weight of one or more elements of the lanthanides.

2. A process as claimed in claim 1, wherein the catalytically active mass of the catalyst comprises from 90 to 99.9% by weight of zirconium oxide and from 0.1 to 10% by weight of lanthanum, cerium, praseodymium, neodymium, samarium, europium or mixtures thereof.

3. A process as claimed in claim 1, wherein the catalytically active mass of the catalyst comprises from 92 to 99% by weight of zirconium oxide and from 1 to 8% by weight of lanthanum(III) oxide.

4. A process as claimed in claim 1, wherein the zirconium oxide is monoclinic zirconium dioxide.

5. A process as claimed in claim 1, wherein the carboxylic acid or ester used is pivalic acid or ester, isobutyric acid or ester, or cyclohexanecarboxylic acid or ester.

6. A process as claimed in claim 1, wherein the molar ratio of hydrogen to carboxylic acid or ester is within the range from 2:1 to 100:1.

7. A process as claimed in claim 1, wherein the reaction is carried out in a fixed bed.

8. A process as claimed in claim 1, wherein said catalytically active mass consists essentially of from 80 to 99.9% by weight of zirconium oxide and from 0.1 to 20% by weight of one or more elements of the lanthanides.

9. A process as claimed in claim 8, wherein the zirconium oxide is monoclinic zirconium dioxide.

* * * * *